(12) United States Patent
Woizenko et al.

(10) Patent No.: US 10,421,073 B2
(45) Date of Patent: Sep. 24, 2019

(54) COVERING DEVICE, IN PARTICULAR LID, FOR COVERING REACTION VESSELS

(71) Applicant: HAMILTON BONADUZ AG, Bonaduz (CH)

(72) Inventors: Eduard Woizenko, Domat/Ems (CH); Sandro Sferlazza, Bonaduz (CH)

(73) Assignee: HAMILTON BONADUZ AG, Bonaduz (CH)

( * ) Notice: Subject to any disclaimer, the term of this patent is extended or adjusted under 35 U.S.C. 154(b) by 0 days.

(21) Appl. No.: 15/105,817

(22) PCT Filed: Dec. 19, 2014

(86) PCT No.: PCT/EP2014/078695
§ 371 (c)(1),
(2) Date: Jun. 17, 2016

(87) PCT Pub. No.: WO2015/091928
PCT Pub. Date: Jun. 25, 2015

(65) Prior Publication Data
US 2016/0310943 A1    Oct. 27, 2016

(30) Foreign Application Priority Data
Dec. 20, 2013  (DE) .......................... 10 2013 114 732

(51) Int. Cl.
*B01L 3/00* (2006.01)
*G01N 35/10* (2006.01)
(Continued)

(52) U.S. Cl.
CPC ......... *B01L 3/50853* (2013.01); *C12M 23/12* (2013.01); *C12M 23/38* (2013.01);
(Continued)

(58) Field of Classification Search
CPC ... B01L 3/50853; C12M 23/12; C12M 23/38; C12Q 1/686; G01N 35/00029; G01N 35/10
(Continued)

(56) References Cited

U.S. PATENT DOCUMENTS

| 5,604,130 A | 2/1997 | Warner et al. |
| 6,159,368 A | 12/2000 | Moring et al. |

(Continued)

FOREIGN PATENT DOCUMENTS

| CN | 102481572 A | 5/2012 |
| DE | 20301279 U1 | 4/2003 |

(Continued)

OTHER PUBLICATIONS

International Search Report cited in PCT1EP2014/078695 dated Mar. 23, 2015, 2 pages.

(Continued)

*Primary Examiner* — Jill A Warden
*Assistant Examiner* — Jacqueline Brazin
(74) *Attorney, Agent, or Firm* — Rothwell, Figg, Ernst & Manbeck P.C.

(57) ABSTRACT

The invention relates to a covering device (10), in particular a lid, for covering reaction vessels (50), in particular PCR plates, microtiter plates, and the like, comprising: a substantially flat main body (14) having an inside (34) and an outside (12), at least one planar sealing element (36) arranged on the main body (14) and connected to the main body, wherein the at least one sealing element (36) is arranged on the inside (34) of the main body (14), an edge segment (16), which runs along the periphery of the main body and extends from the outside (12) in the direction of the inside (34) and beyond the inside, and at least one spring element (22, 24) arranged on the main body (14) or on the (Continued)

sealing element (36), which at least one spring element is designed in such a way that the at least one spring element supports the covering device (10) on a surface (54) of a reaction vessel (50) to be covered facing the covering device (10) in the relaxed state of the at least one spring element and that an intermediate space (56) is formed between the sealing element (36) and the surface (54) of the reaction vessel (50).

17 Claims, 6 Drawing Sheets

(51) Int. Cl.
C12Q 1/68 (2018.01)
G01N 35/00 (2006.01)
C12M 1/00 (2006.01)
C12M 1/32 (2006.01)
C12Q 1/686 (2018.01)

(52) U.S. Cl.
CPC ....... *C12Q 1/686* (2013.01); *G01N 35/00029* (2013.01); *G01N 35/10* (2013.01); *B01L 2200/028* (2013.01); *B01L 2200/0689* (2013.01); *B01L 2300/041* (2013.01); *B01L 2300/046* (2013.01); *B01L 2300/048* (2013.01); *B01L 2300/0809* (2013.01); *B01L 2300/0829* (2013.01); *B01L 2300/0851* (2013.01); *B01L 2300/0858* (2013.01); *B01L 2300/12* (2013.01); *B01L 2300/123* (2013.01); *G01N 2035/00148* (2013.01)

(58) Field of Classification Search
USPC ........................................................ 422/569
See application file for complete search history.

(56) References Cited

U.S. PATENT DOCUMENTS

| 6,309,608 | B1 | 10/2001 | Zhou et al. | |
|---|---|---|---|---|
| 6,486,401 | B1 | 11/2002 | Warhurst et al. | |
| 6,555,792 | B1 | 4/2003 | Elsener et al. | |
| 2003/0044969 | A1* | 3/2003 | Shin | B01L 3/5085 435/288.4 |
| 2005/0019224 | A1* | 1/2005 | Pechter | B01F 5/0085 506/13 |
| 2011/0293488 | A1* | 12/2011 | Nichols | B01L 3/50853 422/500 |
| 2012/0164725 | A1* | 6/2012 | Stettler | B01L 3/50853 435/325 |

FOREIGN PATENT DOCUMENTS

| EP | 0419208 | * | 3/1991 |
|---|---|---|---|
| EP | 0 828 560 | A2 | 3/1998 |
| EP | 1088590 | A1 | 4/2001 |
| EP | 1142795 | A2 | 10/2001 |
| EP | 1 192 995 | A2 | 4/2002 |
| EP | 2415523 | A1 | 2/2012 |
| WO | WO 9423839 | A1 | 10/1994 |
| WO | WO 9527196 | A1 | 10/1995 |
| WO | 96/39481 | A2 | 12/1996 |
| WO | WO 2004067173 | A2 | 8/2004 |

OTHER PUBLICATIONS

International Preliminary Report on Patentability issued in International Patent Application No. PCT/EP2014/078695, 9 pages. (dated Jun. 30, 2016).

Office Action (with English translation) issued in Chinese Patent Application No. 2014800686885, 11 pages. (dated Feb. 4, 2017).

* cited by examiner

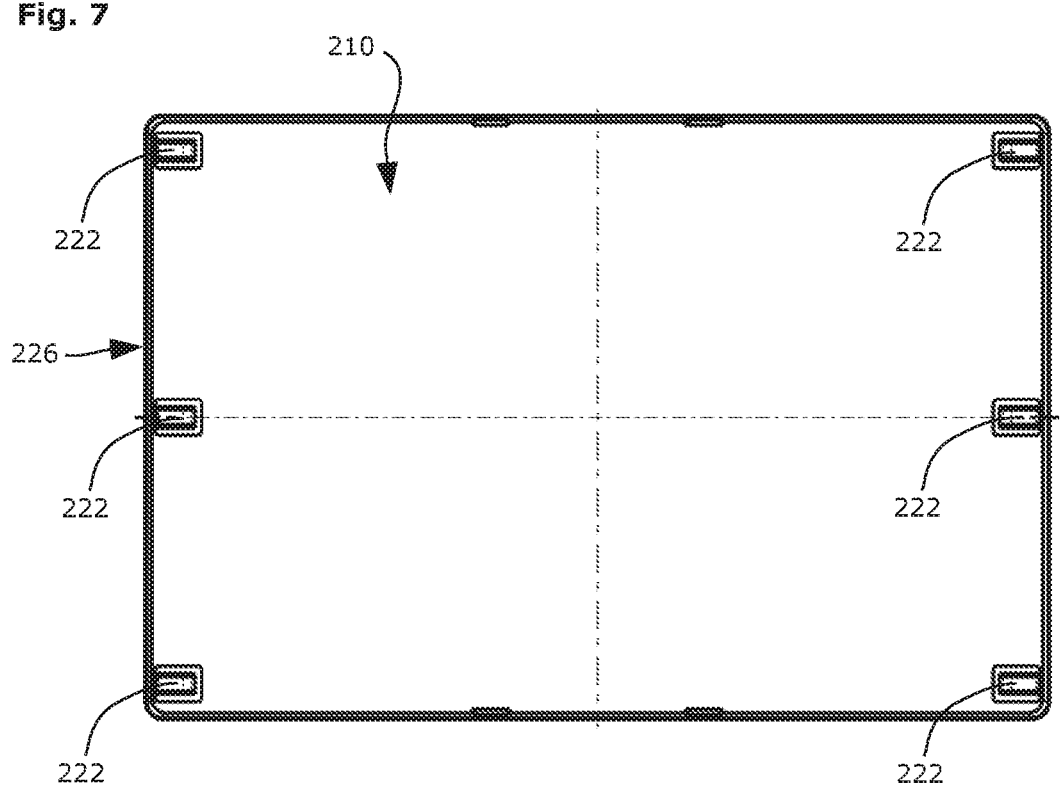

COVERING DEVICE, IN PARTICULAR LID, FOR COVERING REACTION VESSELS

CROSS REFERENCE TO RELATED APPLICATION

This application is a 35 U.S.C. 371 National Phase Entry Application from PCT/EP2014/078695, filed Dec. 19, 2014, which claims the benefit of German Patent Application No. 10 2013 114 732.1 filed on Dec. 20, 2013, the disclosures of which are incorporated by reference in their entirety.

The present invention concerns a covering device, in particular a lid, for covering of reaction vessels, in particular PCR-plates, microtiter plates, and the like.

From EP 1 142 795 A2 a covering mat consisting of an elastic material is known that has a soft lower layer and that is provided with a supporting plate for stiffening. The supporting plate is curved such that it takes a curvature-free form in case of a pressure force applied to the whole area of the supporting plate, in which form the covering mat tightly seals recesses in a reaction vessel. If the pressure onto the supporting plate is reduced, the supporting plate recovers its curved state and is lifted partially from the reaction vessel such that it can be removed from the reaction vessel with little effort.

A further covering device having a curved supporting plate and sidewalls that are laterally arranged and jointly connected thereto is known from EP 1 192 995 A2. If a pressure force is applied onto the curved supporting plate, also this supporting plate takes a curvature-free form, can be fixed by means of the sidewalls that are jointly connected to the supporting plate to a reaction vessel, and can be maintained in the curvature-free form.

The known curved supporting plates having the thereto fixed soft sealing mats have the disadvantage that they adhere due to underpressure generated in the recesses of the reaction vessel to the reaction vessel and are hence only partially released therefrom, when they go over from the curvature-free form to the curved form. Such an adhesion of the covering device is undesired in automated analyzing methods as for example PCR methods, detection methods for viruses or bacteria, or similar methods that are used for bio analytics in research, diagnosis and forensic. Adhesion of covering devices to reaction vessels may lead to an interruption of an entire automatically carried out method. Adhesion of the covering device may also lead to a short-time lift of the reaction vessel itself during releasing, which includes the risk that sample liquid exits from the recesses and that, hence, a mutual contamination of samples occurs.

An object of the invention is to provide a covering device which avoids the aforementioned disadvantages and is, in particular, completely removable from the reaction vessel without adhesion.

In order to solve the problem a covering device is proposed that comprises:
a substantially flat main body having an inside and an outside, at least one planar sealing element arranged on the main body and connected to the main body, wherein the at least one sealing element is arranged on the inside of the main body,
an edge segment which runs along the periphery of the main body and extends from the outside in the direction of the inside and beyond the inside, and
at least one spring element arranged on the main body or on the sealing element such that the at least one spring element supports the covering device on a surface of a reaction vessel to be covered facing the covering device in the relaxed state of the at least one spring element and that an intermediate space is formed between the sealing element and the surface of the reaction vessel.

The relaxed state of the spring element may be called the basic state of the spring element. The spring element takes this form, if the covering device is arranged pressure-free on the reaction vessel, due to which arrangement a distance between the sealing element and the surface of the reaction vessel is provided. This pressure-free arrangement occurs in analysis methods typically before and after the execution of reaction steps, during which the recesses in the reaction vessel have to be closed. In particular, this basic state occurs directly after disposing the covering device onto the reaction vessel and immediately after removing the covering device from the reaction vessel. As the main body is formed substantially flat and not curved, the spring element is able to keep the main body having the thereto arranged sealing element at the distance to the reaction vessel.

Further, it is proposed to form the spring element such that in a strained state the sealing element rests on the surface of the covered reaction vessel, in order to tightly seal sample containers that are arranged in the sampling vessel and preferably formed as recesses or cavities.

If pressure is applied from its outside to the main body, the covering device can be pressed under deformation and pre-tension of the spring element against the surface of the reaction vessel, in order to tightly seal the recesses of the reaction vessel. Preferably, the pressure is applied to the main body or the covering device by a device lid that also may comprise a heating element, when the device lid is or has been closed. For example, the device lid may be the device lid of a thermo block or a thermo cycler.

If the pressure applied to the main body or the covering device is released, the previously deformed and pre-tensioned spring element relaxes and takes its relaxed state (basic state), due to which the flat main body is lifted together with the sealing element arranged thereon from the reaction vessel, since the spring element supports itself on the surface of the reaction vessel. Differently stated, the covering device moves relative to the reaction vessel because of the relaxing spring element.

The spring element may be fixed with at least one end to the main body and/or the edge segment, and may be preferably formed integrally with the main body and/or the edge segment. To this end, it is further proposed that the spring element is formed bent at least in sections having at least one convex and/or concave curvature with respect to the inside of the main body.

The spring element may further be formed as leaf-spring-like strut that is fixed single-sided or double-sided to the main body and/or the edge segment. Here, the leaf-spring-like strut may be fixed single-sided to the edge segment or the main body and may have one movable free end.

Alternatively, it is proposed that the leaf-spring-like strut is fixed double-sided on the main body or the sealing element and the strut comprises several wave-like curvatures between the two fixing regions.

To allow a deflection of the spring element in its strained state it is proposed that the main body comprises at least one spring opening that is assigned to a spring element and formed such that in its strained state the spring element is at least partially contained therein, in particular with the freely movable end of the spring element.

It is preferred that the covering device comprises at least two spring elements, preferably an even number of spring elements. Here, the spring elements may be arranged in distributed manner along the periphery of the main body.

Providing two or more, in particular an even number of spring elements, allows a uniform support of the covering device on the reaction vessel. Further, pre-tension forces of the single spring elements act together as a total pre-tension force on the covering device such that it can be lifted uniformly from a covered reaction vessel after releasing the applied pressure. An even number of spring elements is preferable in particular for reaction vessels or covering devices which have a polygonal, in particular a rectangular, elementary form. For other elementary forms such as a circle or a different polygon (for example a hexagon) also three spring elements may be used. In this connection it should be noted that also a single spring element may be sufficient. For example, for a rectangular elementary form of the covering device a spring element is conceivable that is arranged on one side such that the covering device rests in the relaxed state of the spring element on the reaction vessel inclined to its surface. Conceivable is also a single, centrally arranged spring element for an according design of the reaction vessel.

Further, it is proposed that the edge segment comprises an upper rim adjacent to the main body and a lower rim connected to the upper rim, wherein a circumference measured along the upper rim is smaller than the circumference along the lower rim. Here, the upper rim and the lower rim may be connected by a step-like, circumferential protrusion, which is inclined, preferably substantially orthogonal, to the upper and the lower rim. To this end, it is further proposed that the lower rim and the step-like protrusion are dimensioned such that the covering device is stackable on a further similar covering device, wherein in the stacked state the covering device rests with its lower rim on the step-like protrusion of the further covering device arranged thereunder.

An edge segment formed in this manner having rims that are arranged step-like with respect to each other allows a simple, jam-free stacking of covering devices with low friction. Stacking of covering devices is in particular important during packing of the devices, as the packing density can be increased. Further, a stack of covering devices having such edge segments needs also less space in an analysis or dosing device for automated carrying out of analysis methods.

In order to improve the automated use of covering devices it is further proposed that in the edge segment, preferably in the upper rim, coupling means are provided, to take up the covering device releasable by means of a gripping device and to transport it, wherein the coupling means are preferably formed as openings in the edge segment into which corresponding lobes of the gripping device can be inserted.

Preferably, the main body comprises two parallel longitudinal sides and two parallel transversal sides, wherein the spring elements are arranged along the longitudinal sides and/or along the transversal sides, preferably regularly distributed along the longitudinal sides and/or along the transversal sides. Here, along the two longitudinal sides may for example be used spring elements that are designed or formed differently than those used along the two transversal sides. Further, also the number of spring elements along the longitudinal sides and along the transversal sides may be different.

To achieve a desired stiffness of the flat main body and a fatigue-free pre-tension of the spring elements of the covering device, it is proposed that the main body, the edge segment, and the spring elements are manufactured from a plastic material, preferably from an injection moldable plastic material, such as polycarbonate (PC), polymer blends (ASB-PC), polyamide (PA) or polybutylenterephtalat (PBT), wherein the main body, the edge segment, and the spring elements are formed preferably integrally. The sealing element (36) may be formed from a thermoplastic elastomer (TPE) or from a silicone containing elastomer.

The width of the main body between its outside and its inside is preferably about 0.5 to 3.0 mm, in particular about 1.0 to 2.0 mm. Due to this, a sufficient stiffness of the main body is achieved. The width of the sealing element is preferably about 0.5 to 3.0 mm, in particular about 1.0 to 2.0 mm. Due to this, a reliable sealing of the recesses of the reaction vessel is achieved, if the covering device is pressed onto the reaction vessel.

The invention concerns further a reaction vessel, in particular a PCR plate or a microtiter plate, comprising several recesses or cavities as sample containers, wherein the reaction vessel is covered with a covering device that comprises at least one of the features described above, wherein the reaction vessel is preferably formed according to the ANSI standards ANSI/SLAS 1-2004 to ANSI/SLAS 4-2004.

Preferably, hence, microtiter plates having a dimension of, wherein 96, 384, . . . recesses or cavities or wells are provided, into which the sample liquid can be filled.

The invention concerns further also a method for covering reaction vessels, comprising the steps:
a) providing a stack comprising several covering devices, which comprise at least one of the features describes above;
b) providing at least one reaction vessel to be covered, in particular a PCR plate or a microtiter plate;
c) taking up an uppermost covering device of the stack by means of a gripping device;
d) moving the taken covering device to the or to a reaction vessel to be covered;
e) placing the taken covering device onto the reaction vessel;
f) applying pressure to the covering device on the reaction vessel under deformation and pre-tension of the spring elements of the covering device, in order to tightly seal recesses in the reaction vessel by means of the sealing element;
g) carrying out the steps necessary for a desired analysis method with closed reaction vessels, such as increasing and/or lowering a temperature;
h) releasing the covering device by decreasing the applied pressure under recovery and relaxation of the spring elements in order to release the sealing element completely from the reaction vessel;
i) taking up the used covering device by means of the gripping device and disposing of the covering device.

In the method the steps a) to e) may be carried out repeatedly such that several reaction vessels are covered consecutively with corresponding covering devices, wherein the steps f) to h) are preferably carried out simultaneously for all covered reaction vessels and wherein preferably the step i) is carried out repeatedly until all used covering device are removed from the respective reaction vessels.

In step i) it is further conceivable that this step also comprises stacking of the used covering devices in order to increase the packing density of the materials to be disposed of as much as possible.

Altogether the method is directed to a highly automated use of covering devices in the context of automated analysis methods, wherein the covering devices comprising the spring elements as described above make a substantial contribution to a reliable automatization. Further, also the simple stackability of the covering devices, which is achieved by the design of the edge, serves an improved automatization.

The method is carried out preferably by an automated dosing device, in particular by a pipetting robot.

Finally, the invention concerns also a dosing device, in particular a pipetting robot, comprising:

a support plate onto which a stack of non-used covering devices that comprise at least one of the aforementioned features is positioned and onto which at least one reaction vessel is positioned, and a gripping device, which is movable relative to the support plate in three main directions and configured to take up covering devices from the stack and to place them onto the reaction vessel, as well as to remove a used covering device from a reaction vessel and to dispose of the used covering device.

In the following the invention will be described under reference to the accompanying figures in an exemplary and non-limiting manner.

FIG. 7 shows schematically and simplified a third embodiment of a covering device in a top view.

Figure 1:
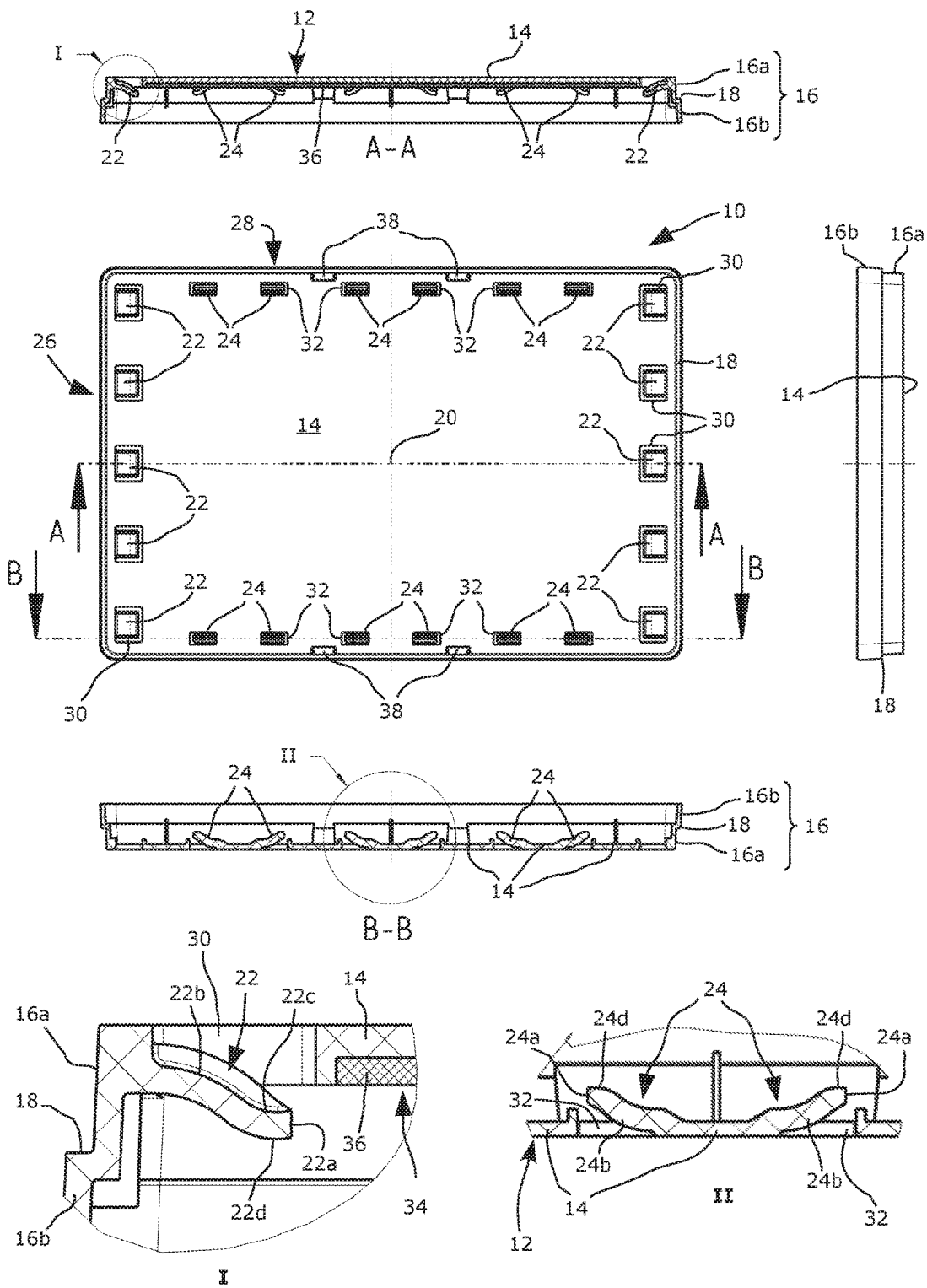
FIG. 1 shows schematically and simplified a first embodiment of a covering device in a top view, in according sectional views along the sectional lines A-A and B-B, and enlarged sectional regions I and II, and in a lateral elevation.

In FIG. 1 a covering device 10 according to a first embodiment is illustrated in top view with line of sight onto the outside 12 and in corresponding sectional views according to the sectional lines A-A, B-B, and enlargements I and II. Further, a lateral elevation is illustrated. The description of the covering device is made under simultaneous reference to the different views, without that this is explicitly mentioned every time.

The covering device comprises a main body 14 and an edge segment 16 that comprises an upper rim 16a and a lower rim 16b. The two rims 16a and 16b are connected with each other by means of a protrusion or a step 18, wherein the lower rim 16b has a larger distance to a center 20 of the covering device than the upper rim 16a. Stated differently, the upper rim 16a has a smaller circumference than the lower rim 16b.

The covering device 10 comprises several spring elements 22 and 24, wherein the spring elements 22 are provided along the transversal sides 26 and the spring elements 24 are provided along the longitudinal sides 28 of the covering device, respectively. Further, in the top view and the sectional views spring openings 30 and 32 are illustrated, which are formed in the main body. The main body 14 comprises a sealing element 36 on its inside 34, which is preferably formed from a softer material than the main body 14.

The spring elements 22 are arranged in a distributed manner along the transversal sides 26 and are fixed to the edge segment 16, in particular to the upper rim 16a, or are formed integrally with the edge segment 16 (sectional enlargement I). The spring element 22 is therefore fixed in the region of the edge segment 16 in the manner of a clamping and comprises a movable free end 22a. The spring element 22 may be formed as bent, in particular leaf-spring-like, strut having convex (22b) and concave (22c) curvatures with respect to the inside 34 of the main body 14. The spring element 22 comprises further a supporting region 22d, which serves for supporting the covering device 10 on a reaction vessel 50, which will be described later with reference to FIGS. 2 and 3.

The spring elements 24 are arranged distributed along the longitudinal side 28 and are fixed to the main body 14 or formed integrally with the main body (sectional enlargement II). The spring elements 24 comprise also movable free ends 24a and are connected to the main body 14 in the manner of a clamping. Further, the spring elements 24 comprise supporting regions 24d, which serve for supporting the covering device 10 on the reaction vessel 50, which will be described later with reference to FIGS. 2 and 3. Just like the spring elements 22 also the spring elements 24 can be formed with convex or concave curvatures 24b or 24c.

The forms of the spring elements 22 and 24 that have bent or curved sections 22b, 22c, 24b, 24c, which are illustrated here, are preferred embodiments. Alternatively, the spring elements may also be formed substantially straight, wherein they are inclined in this case with respect to the inside of the main body 14.

According to this embodiment the spring elements 22, 24 are arranged in a distributed manner along the periphery of the main body 14 or the covering device 10. The spring elements 22 are arranged in a regularly distributed manner along the two transversal sides 26. The spring elements 24 are arranged in a regularly distributed manner along the two longitudinal sides 28.

The covering device 10 comprises further coupling means 38, which are formed here as coupling openings 38. The coupling means are preferably provided on the upper rim 16a. Corresponding lobes of a gripping device that is not illustrated here can be inserted into the coupling openings 38 to take the covering device 10 up, to transport it and to place it on a desired position.

The covering device 10 is provided to cover a reaction vessel 50 (FIG. 2) such as a PCR plate, a microtiter plate or other such reaction vessels, and to tightly seal the reaction vessel during a desired time during one or several reaction steps of an analysis method. Further, the reaction vessels 50 to be covered are typically rectangular microtiter plates. These are typically formed from plastic materials such as polystyrene, polyvinyl chloride or, for specific applications, also from glass. In the reaction vessel 50 recesses 52, which are separated or isolated from each other, are arranged, which are also called wells or cavities. The recesses 52 are typically arranged in rows and columns. The standardization of such microtiter plates is based on ANSI standards (ANSI/SBS 1-2004, ANSI/SBS 2-2004, ANSI/SBS 3-2004, ANSI/SBS 4-2004). The exact dimensions of such standardized microtiter plates (length×width×height) are according to ANSI standards 127.76 mm×85.48 mm×14.35 mm. For such microtiter plates or reaction vessels there is a large number of designs with different numbers of recesses 52, wherein these different microtiter plates have usually the same basic area, but possibly different heights.

The main body 14 is preferably substantially flat and preferably formed stiff and from a plastic material. The sealing element 36 is also formed from a plastic material and connected in a fixed manner to the inside 34 of the main body 14. Regarding possible materials and widths of the main body 14 and the sealing elements 36 reference is made to the introductory part of the description and to the claims.

Figure 2:
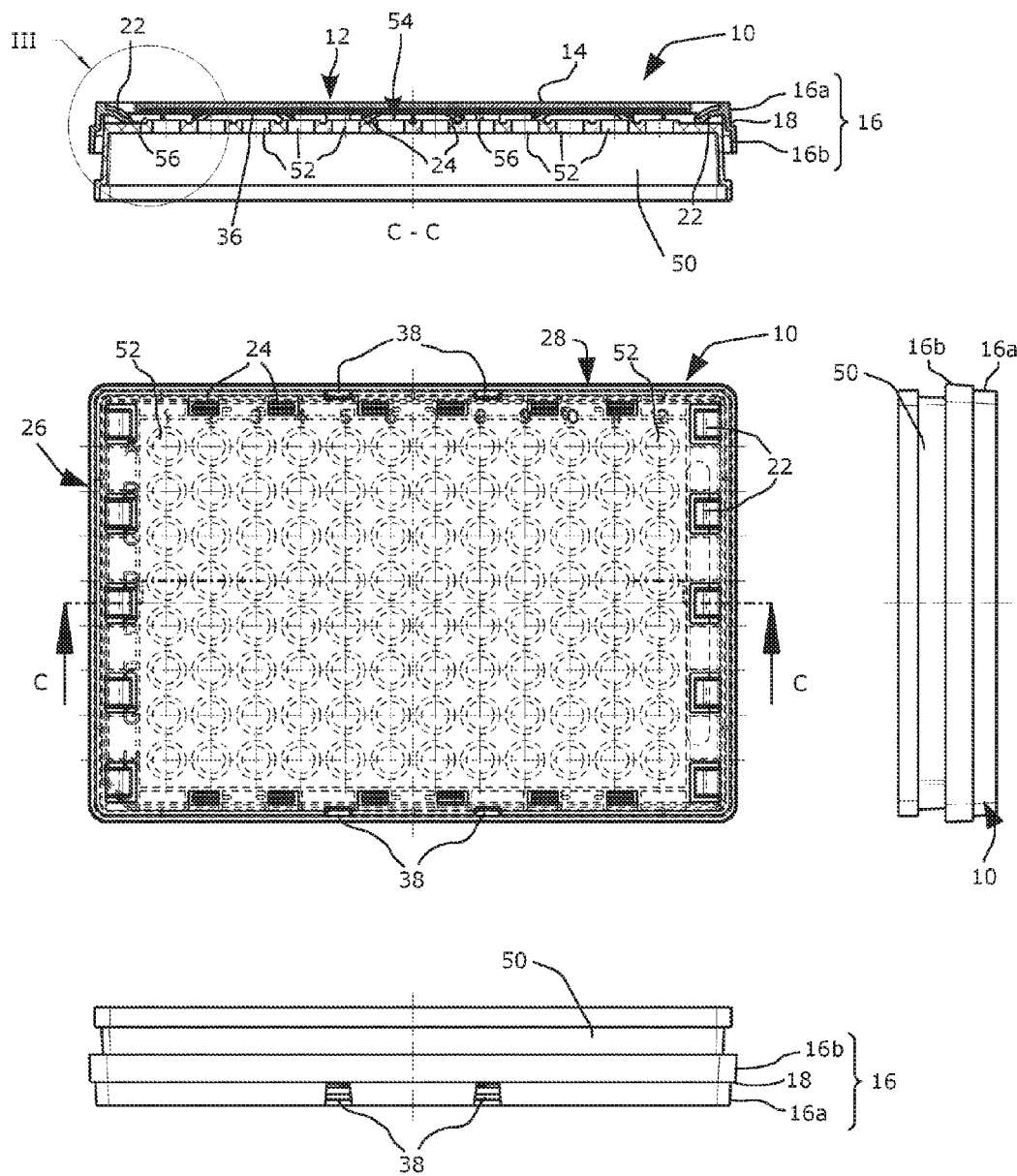
FIG. 2 shows schematically and simplified the first embodiment of a covering device with a reaction vessel arranged thereunder in a top view, a sectional view according to the sectional line C-C, as well as two lateral elevations of a longitudinal side and a transversal side.

FIG. 2 shows in a top view and a corresponding sectional view according to the sectional line C-C and lateral elevations a reaction vessel 50, which comprises for example 96 recesses 52 onto which a covering device 10 according to the first embodiment (FIG. 1) is arranged. The recesses 52 or further components of the reaction vessel 50 are illustrated in the top view in broken lines, as they are arranged below the covering device 10. It should be noted that in FIG. 2 also reference signs are contained, which have already been described with reference to FIG. 1, in order to allow a simple reference to the same elements without a repeated description.

From the sectional view according to the sectional line C-C it can be seen that the covering device 10 rests by means of its spring elements 22, 24, in particular by means of their supporting regions 22d, 24d (FIG. 1, I and II), on a surface 54 of the reaction vessel 50. In the state illustrated here showing relaxed spring elements 22, 24 a distance or intermediate space 56 between the surface 54 of the reaction vessel 50 and the sealing element is formed such that the recesses 52 are not (yet) tightly sealed.

This state with relaxed spring elements 22, 24 is also illustrated in a slightly increased sectional view according to the sectional line C-C of FIG. 2 in FIG. 3a and a corresponding sectional enlargement III (exemplary for the spring elements 22). In FIG. 3b the covering device 10 is illustrated in a so-called sealing position. Here, a uniform pressure P is applied to the covering device on its outside 12. By this pressure P the covering device 10 is moved relative to the reaction vessel 50, in particular it is moved towards the surface 54 of the reaction vessel until the covering device 10 rests with its sealing element 36 on the surface 54, in particular on opening rims 54a of the recesses 52 belonging to the surface 54, such that the recesses 52 are tightly sealed. During this movement of the covering device 10 into the direction of the surface 54 of the reaction vessel 50 the spring elements 22, 24 are deformed or pre-tensioned. In this process, the spring elements are deflected in the direction of the spring openings 30 or 32 and will be contained at least partially in this spring openings 30, 32. The pressure P is for example generated by a device lid of a thermo cycler or a thermo block, in which the reaction vessel 50 and the covering device 10 are accommodated. The tight sealing of the recesses 52 serves in this process in particular to guarantee that the sample liquid contained in the recesses 52 does not escape or evaporate during a temperature change (heating) necessary in an analysis method.

If the applied pressure decreases, the spring elements 22, 24 relax, due to which the covering device 10, in particular the main body 14 and the sealing element 36 fixed thereto are lifted simultaneously and completely from the surface 54 or the edge regions 54a such that the state according to FIG. 3a (enlargement III) is again achieved. In this process, the pre-tension force caused by the spring elements 22, 24 and the flat or stiff design of the main body allows overcoming of underpressure that was possibly generated in the recesses 52, which could cause adhesion of the sealing element 36 to the surface 54. The covering device 10 rests therefore again in a released state with relaxed spring elements 22, 24 on the reaction vessel without being adhered to the reaction vessel and can be lifted simply and preferably in automated manner and can be removed from the reaction vessel.

Figure 4:
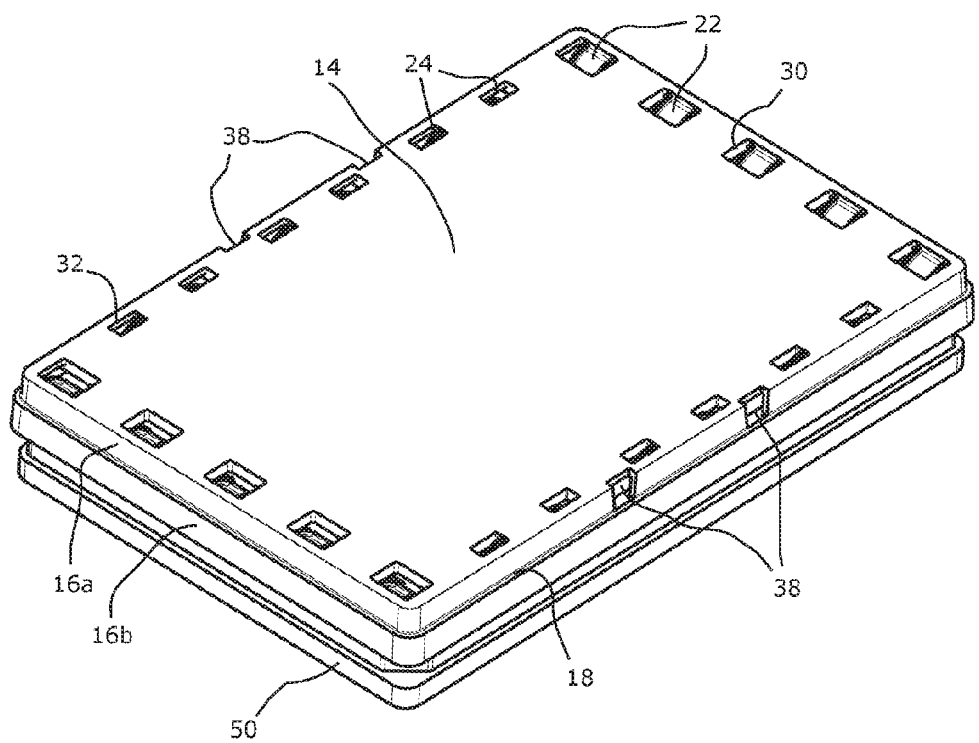
FIG. 4 shows a perspective view of the covering device according to the first embodiment together with the reaction vessel.

FIG. 4 illustrates in perspective view the covering device 10 and the reaction vessel 50. In this view, in particular, the coupling openings 38 can be seen due to which the covering device 10 can be gripped by means of a gripping device and lifted and removed from the reaction vessel 50. Further, from this view, in particular in combination with the enlarged sectional view I of FIG. 1, the step-like protrusion 18 of the circumferential edge segment 16 can be seen. This step-like protrusion has the advantage that several covering devices 10-1 to 10-5 can be arranged on top of each other as stack 60, as can be seen from FIG. 5. The step-like protrusion 18 is dimensioned such that an upper covering device 10-1 is supported on its lower rim 16b on the step-like protrusion 18 of a covering device 10-2, which is arranged directly below. As the rims 16a and 16b of a covering device 10-1 to 10-5 constitute approximately each the half of the total height of the edge segment 16, the packing density of a stack of covering devices 10 can be approximately doubled. Adding of covering devices 10-1 to 10-5 to a stack 60 and also lifting of a topmost covering device 10-1 from the stack 60 is further supported by rims 16a and 16b that are slightly inclined with respect to a vertical. Differently stated, an angle between the rims 16a and 16b and a plane of the main body is slightly larger than 90°, but preferably smaller than 100°. Accordingly, also the step-like protrusion 18 is substantially orthogonal to the rims 16a, 16b. Preferably, the step-like protrusion 18 is included in a plane parallel to the main body 14, but may also be slightly inclined with respect to such a plane. As in the stack 16 the covering devices 10-1 to 10-5 rest on their respective lower rims 16b, the spring elements 22, 24 are not deformed in the stacked state and can therefore be stored in their relaxed state such that the risk of a plastic deformation of the spring elements 22, 24 due to long-term acting forces can be excluded.

Figure 5:
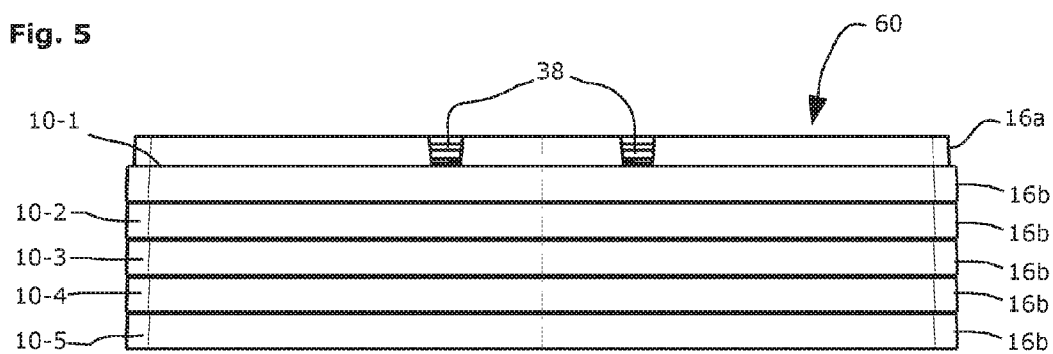
FIG. 5 shows schematically and simplified a stack of covering devices in a lateral elevation.

A stack 60 as shown in FIG. 5 may of cause comprise more or less than the five illustrated covering devices 10-1 to 10-5. Using such covering devices 10 allows, according to the space available in an automated analysis device, also using several stacks from which covering devices 10 for covering and sealing of reaction vessels 50 can then be taken continuously. The covering devices 10 are preferably used as one way consumable material and are disposed of after covering/sealing of a reaction vessel to avoid involved cleaning and the risk of contamination.

Using such a stack 60 a method for covering of reaction vessels can be carried out that may comprise the following steps:

a) providing a stack 60 comprising several covering devices 10-1 to 10-5 b) providing at least one reaction vessel 50 to be covered, in particular a PCR plate or a microtiter plate;

c) taking up the uppermost covering device 10-1 of the stack 60 by means of a gripping device not illustrated here;

d) moving the taken covering device 10-1 to the or to a reaction vessel 50 to be covered;

e) placing the taken covering device 10-1 onto the desired reaction vessel 50;

f) applying pressure to the covering device 10-1 on the reaction vessel 50 under deformation and pre-tension of spring elements 22, 24 of the covering device 10-1, in order to tightly seal the recesses 52 in the reaction vessel 50 by means of the sealing element 36;

g) carrying out the steps necessary for a desired analysis method with closed reaction vessels 50, such as temperature increase and/or decrease;

h) releasing the covering device 10-1 by decreasing the applied pressure under recovery and relaxation of the spring elements 22, 24, in order to release the sealing element 36 completely from the reaction vessel 50;

i) taking up the used covering device 10-1 by means of the gripping device and disposing of the covering device 10-1.

In such a method the steps a) to e) may be carried out repeatedly such that several reaction vessels are covered consecutively with further respective covering devices 10-2 to 10-5 preferably from the stack 60. The steps f) to h) may also be carried out simultaneously for several or all covered reaction vessels. Finally, the step i) may be carried out repeatedly until all used covering devices 10-2 to 10-5 are removed from the respective reaction vessels.

Figure 3:
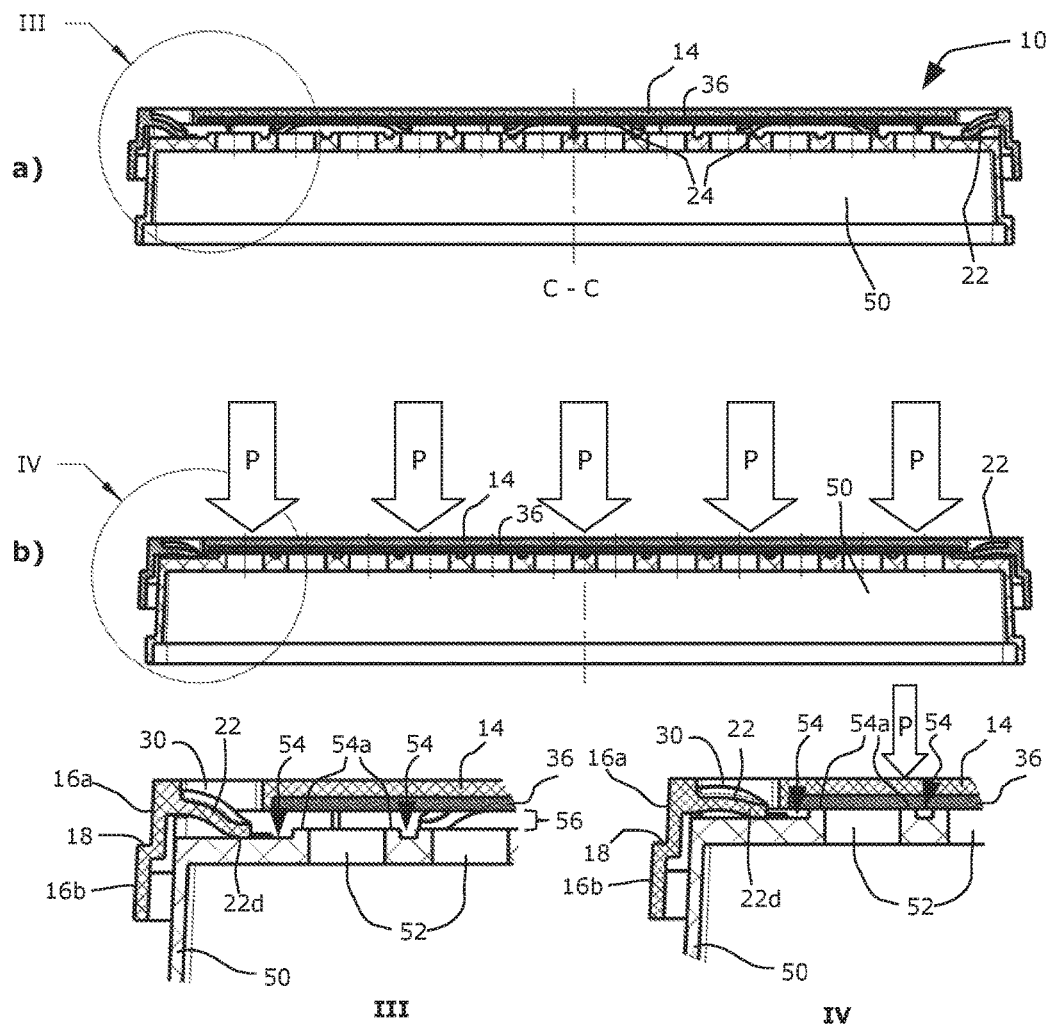
FIG. 3 shows in sub-figures a) and b) sectional views corresponding to the sectional line C-C of FIG. 2, wherein sub-figure a) shows the covering device with relaxed spring elements on top of the reaction vessel and wherein sub-figure b) shows the covering device with strained spring elements on the reaction vessel, and corresponding enlargements of the sections III and IV.
Figure 6:
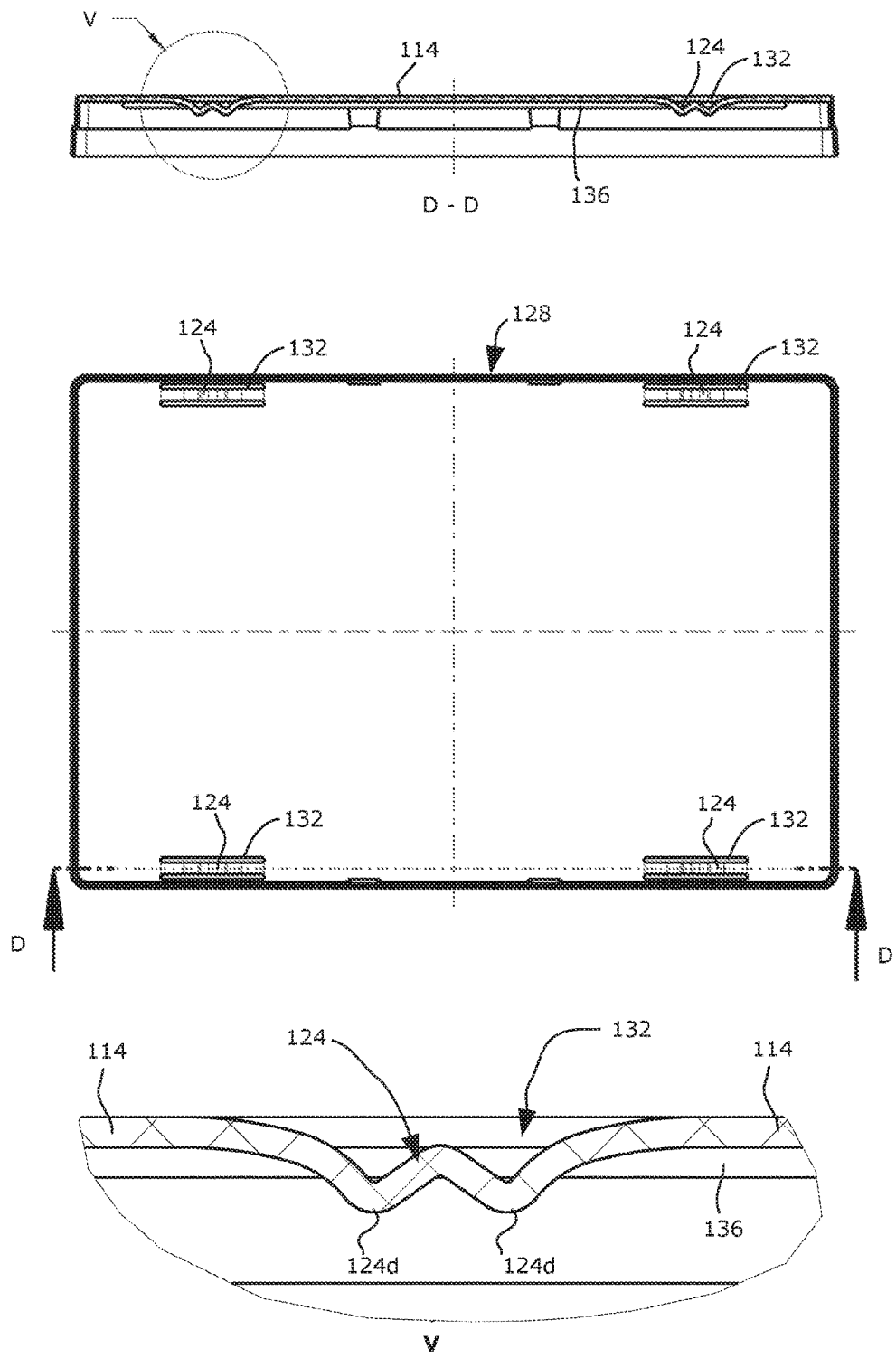
FIG. 6 shows schematically and simplified a second embodiment of a covering device in a top view, a corresponding sectional view according to sectional line D-D and an enlarged sectional region V.

FIG. 6 illustrates a second embodiment of a covering device 110 comprising spring elements 124, which are fixed to the main body 114 along the longitudinal sides 128. The spring elements 124 are formed in the manner of wave-like struts and comprise two supporting regions 124*d*, by means of which they can rest on the surface 54 of a reaction vessel 50 (FIGS. 2 and 3). The spring elements 124 are connected double-sided to the main body 114 and do not have free ends. Due to the wave-like design, however, these spring elements 124 can also be deformed and pre-tensioned, if pressure is applied to the main body 114. The spring elements 124 move then at least partially into corresponding spring openings 132 in the main body 114.

Of course also in this embodiment a sealing element 136 is connected with the main body 114. Otherwise, functioning and use of the covering device 110 is the same as of the covering device 10 of FIGS. 1 to 4. Also the covering device 110 has a design (edge segment) like the first embodiment according to which several covering devices 110 can be arranged on top of each other as stack.

Finally, FIG. 7 illustrates a third embodiment of a covering device 210 comprising a smaller number of spring elements 222 along the transversal sides 226 of the covering device. In comparison with those of FIG. 1 the spring elements 222 are formed more longitudinal, but have in principal the same functions and effects. Also this embodiment is stackable and comprises an edge segment which is identical or similar to the first embodiment.

For all embodiments the width of the main body 14 is about 0.5 to 3.0 mm, in particular about 1.0 to 2.0 mm, and the width of the sealing element 36 is about 0.5 to 3.0 mm, in particular about 1.0 to 2.0 mm. Taking the synopsis of the different embodiments, it is further clear that the design of the spring elements and their arrangement in the main body or their number can be changed and adjusted. It is shown that for covering devices that have a substantially rectangular elementary form an even number of spring elements is advantageous, in order to be able to arrange them symmetrically and in order to achieve a uniform action of the spring elements onto the main body or the covering device, in particular, if the spring elements are moved from their pre-tensioned state into the relaxed state.

The covering devices described in here are preferably used in automatically working analysis or dosing devices, such as pipetting robots. Such analysis or dosing devices comprise typically according driving and controlling means that allow carrying out the method steps described above under use of the aforementioned covering devices, including taking up and transporting of such covering devices. In this process, for automated handling preferably the same gripping device may be used that is also used for taking up and transporting reaction vessels.

The invention claimed is:

1. A covering device (10) for covering reaction vessels (50) comprising:
   a substantially flat main body (14) having an inside (34) and an outside (12),
   at least one planar sealing element (36) arranged on the main body (14) and connected to the main body (14), wherein the at least one sealing element (36) is arranged on the inside (34) of the main body (14),
   an edge segment (16), which runs along the periphery of the main body and extends from the outside (12) in the direction of the inside (34) and beyond the inside, and
   at least one spring element (22, 24; 124; 222) arranged on the main body (14) or on the sealing element (36), wherein the at least one spring element in a relaxed state supports the covering device (10) on a surface (54) of a reaction vessel (50) to be covered facing the covering device (10) such that an intermediate space (56) is formed between the sealing element (36) and the surface (54) of the reaction vessel (50),
   wherein the spring element (22, 24; 124; 222) in a strained state rests on the surface (54) of the covered reaction vessel (50) to tightly seal sample containers (52) that are arranged in the sampling vessel,
   wherein the spring element (22, 24; 124; 222) is formed as leaf-spring-like strut that is fixed single-sided or double-sided to the main body (14) and/or the edge segment (16),
   wherein the main body (14) comprises at least one spring opening (30, 32; 132) formed through the main body, and each spring opening (30, 32; 132) is assigned to a respective spring element (22, 24; 124; 222) such that the respective spring element (22, 24; 124; 222) in the strained state is contained at least partially in the spring opening (30, 32; 132).

2. The covering device according to claim 1, wherein the leaf-spring-like strut (22, 24) is fixed single-sided to the edge segment (16) or the main body (14) and has a movable free end (22*a*, 24*a*).

3. The covering device according to claim 1, wherein the leaf-spring-like strut (124) is fixed double-sided on the main body (114) or the sealing element and the strut (124) comprises several wave-like curvatures (124*d*) between the two fixing regions.

4. The covering device according to claim 1, wherein the covering device comprises at least two spring elements (22, 24; 124; 222).

5. The covering device according to claim 4, wherein the spring elements (22, 24; 124; 222) are arranged in a distributed manner along the periphery of the main body (14).

6. The covering device according to claim 1, wherein the edge segment (16) comprises an upper rim (16*a*) adjacent to the main body (14) and a lower rim (16*b*) connected to the upper rim (16*a*), wherein a circumference measured along the upper rim (16*a*) is smaller than the circumference along the lower rim (16*b*).

7. The covering device according to claim 6, wherein the upper rim (16*a*) and the lower rim (16*b*) are connected with each other by means of a step-like circumferential protrusion (18), which is inclined, preferably substantial orthogonal, with respect to the upper and the lower rim (16*a*, 16*b*).

8. The covering device according to claim 7, wherein the lower rim (16*b*) and the step-like protrusion (18) are dimensioned such that the covering device (10-1) is stackable on a further similar covering device (10-2), wherein in the stacked state the covering device (10-1) rests with the lower rim (16b) on the step-like protrusion (18) of the further covering device (10-2) arranged thereunder.

9. The covering device according to claim 1, wherein coupling openings (38) are provided in the edge segment (16) into which corresponding lobes of a gripping device can be inserted to releasable take up and transport the covering device (10) by a gripping device.

10. The covering device according to claim 1, wherein the main body (14) comprises two parallel longitudinal sides (28) and two parallel transversal sides (26), wherein the spring elements (22, 24; 124; 222) are arranged along the longitudinal sides (28) and/or along the transversal sides (26).

11. The covering device according to claim 1, wherein the main body (14), the edge segment (16), and the spring elements (22, 24; 124; 222) are formed integrally from a plastic material, and wherein the sealing element (36) is formed from a thermoplastic elastomer (TPE) or a silicone containing elastomer.

12. The covering device according to claim 1, wherein the width of the main body (14) between its outside (12) and its inside (34) is about 0.5 to 3.0 mm, and wherein the width of the sealing element (36) is about 0.5 to 3.0 mm.

13. A reaction vessel (50) comprising several recesses (52) or cavities as sample containers, wherein the reaction vessel (50) is covered with a covering device (10) according to claim 1, wherein the reaction vessel (50) is formed according to the ANSI standards ANSI/SLAS 1-2004 to ANSI/SLAS 4-2004.

14. The covering device according to claim 1, wherein the spring element (22, 24; 124; 222) comprises a movable free end (22a, 24a), and each spring element (22, 24; 124, 222) is configured such that in the strained state the movable free end (22a, 24a) is contained in the spring opening (30, 32; 132).

15. The covering device according to claim 1, wherein one end of the at least one spring element (22, 24; 124; 222) is integrally fixed with either the main body (14) or the edge segment (16).

16. The covering device according to claim 15, wherein the spring element (22, 24; 124; 222) is formed bent at least in sections with at least a convex and/or concave curvature (22b, 22c, 24b) with respect to the inside (34) of the main body (14).

17. The covering device according to claim 15, wherein the one end of the at least one spring element (22, 24; 124; 222) is formed integrally with the main body (14) and/or the edge segment (16).

\* \* \* \* \*